(12) United States Patent
Tovey et al.

(10) Patent No.: US 12,359,195 B2
(45) Date of Patent: Jul. 15, 2025

(54) SECRETED REPORTER-PEPTIDES FOR OPTIMIZING CELL-BASED ASSAYS FOR ANALYSIS ON IMMUNO-ASSAY PLATFORMS

(71) Applicant: SVAR Life Science AB, Malmö (SE)

(72) Inventors: Michael Tovey, Paris (FR); Christophe Lallemand, Paris (FR); Benoit Vallette, Villejuif (FR); Lue Huang, Paris (FR)

(73) Assignee: SVAR LIFE SCIENCE AB, Malmö (SE)

( * ) Notice: Subject to any disclaimer, the term of this patent is extended or adjusted under 35 U.S.C. 154(b) by 1136 days.

(21) Appl. No.: 16/758,694

(22) PCT Filed: Oct. 25, 2018

(86) PCT No.: PCT/EP2018/079292
§ 371 (c)(1),
(2) Date: Apr. 23, 2020

(87) PCT Pub. No.: WO2019/081643
PCT Pub. Date: May 2, 2019

(65) Prior Publication Data
US 2022/0315919 A1    Oct. 6, 2022

(30) Foreign Application Priority Data
Oct. 27, 2017   (EP) .................................... 17198818

(51) Int. Cl.
*C12N 15/11* (2006.01)
*C12N 15/86* (2006.01)
*C12Q 1/6867* (2018.01)
*C12Q 1/6897* (2018.01)

(52) U.S. Cl.
CPC .............. *C12N 15/11* (2013.01); *C12N 15/86* (2013.01); *C12Q 1/6867* (2013.01); *C12Q 1/6897* (2013.01)

(58) Field of Classification Search
CPC ........ C12N 15/11; C12N 15/86; C12N 15/85; C12Q 1/6867; C12Q 1/6897; G01N 33/5008
See application file for complete search history.

(56) References Cited

FOREIGN PATENT DOCUMENTS

| EP | 1862801 A1 | * | 12/2007 | ......... C12N 15/1086 |
|----|-----------|---|---------|----------------------|
| WO | WO 03060071 A2 | | 7/2003 | |
| WO | WO 2010129503 A1 | | 11/2010 | |
| WO | WO-2015108763 A1 | * | 7/2015 | ........... C12Q 1/6886 |

OTHER PUBLICATIONS

Hörberg J, Moreau K, Tamás MJ, Reymer A. Sequence-specific dynamics of DNA response elements and their flanking sites regulate the recognition by AP-1 transcription factors. Nucleic Acids Res. Sep. 20, 2021;49(16):9280-9293. doi: 10.1093/nar/gkab691. PMID: 34387667; PMCID: PMC8450079. (Year: 2021).*
Bakhos A Tannous et al: "Secreted blood reporters: Insights and applications", Biotechnology Advances, Elsevier Publishing, Barking, GB, vol. 29, No. 6, Aug. 30, 2011 (Aug. 30, 2011), pp.997-1003, XP028306433, ISSN: 0734-9750, DOI: 10.1016/J.BIOTECHADV.201 1.08.021 (Year: 2011).*
Anonymous: "The Oxford Dictionary and thesaurus", The Oxford Dictionary and Thesaurus, Jan. 1, 1997 (Jan. 1, 1997), pp. 1414-1414, XP093186395, ISBN: 978-0-19-860171-5.
Casadevall et al., "pure red-cell aplasia and antierythropoietin antibodies In patients treated with recombinant erythropoietin". Eng. J. Med. 2002, 346:469-475.

(Continued)

*Primary Examiner* — Neil P Hammell
*Assistant Examiner* — Morgan Taylor Lindgren Baltzel
(74) *Attorney, Agent, or Firm* — Lisa Mueller; Casimir Jones SC

(57) ABSTRACT

The present invention relates to small secreted reporter-peptides 15 to 150 amino-acids in length comprising a response element, activated by one or more transcription factors induced by the pharmacology active substance to be analyzed following its interaction with a specific intracellular or cell surface molecule, functionally linked to a response element, a TATA box, a signal peptide, anchor and detection sequences to which antibodies can be raised, and a poy-A tail. The anchor sequence may differ from one peptide to another or may be common to multiple secreted reporter-peptides such that all the peptides can be analyzed simultaneously by ELISA using a detection antibody labelled with for example HRP, or by the use of a commonly available immuno-detection platform such MSD, Gyros, AlphaLisa, or Biacore. The detection sequence is unique to each secreted reporter-peptide and may be labelled with a Sulfo-Tag that permits detection of the peptide on the MSD platform, or Alexa that permits detection on the Gyros platform, or digoxigenin that permits detection of on the PerkinElmer AlphaLISA platform, or left unlabeled for detection by SPR on a Biacore platform. The present invention provides i.a. a substantial improvement of cell-based assays for analysis using automated immune-detection platforms and allows simultaneous analysis of multiple analytes, multiple sampling from a single cell culture, and obviates the necessity to lyse cells and remove cell debris by centrifugation prior to analysis on an automated immuno-detection platform. The present invention also provides a means of increasing the dynamic range, sensitivity and reducing the cost of cell-based assays and can be applied to existing engineered cell lines, such as those containing a reporter-gene such as a luciferase reporter-gene obviating the necessity to extensively re-engineer cell lines containing multiple molecular constructs.

13 Claims, 8 Drawing Sheets

Figure 1:
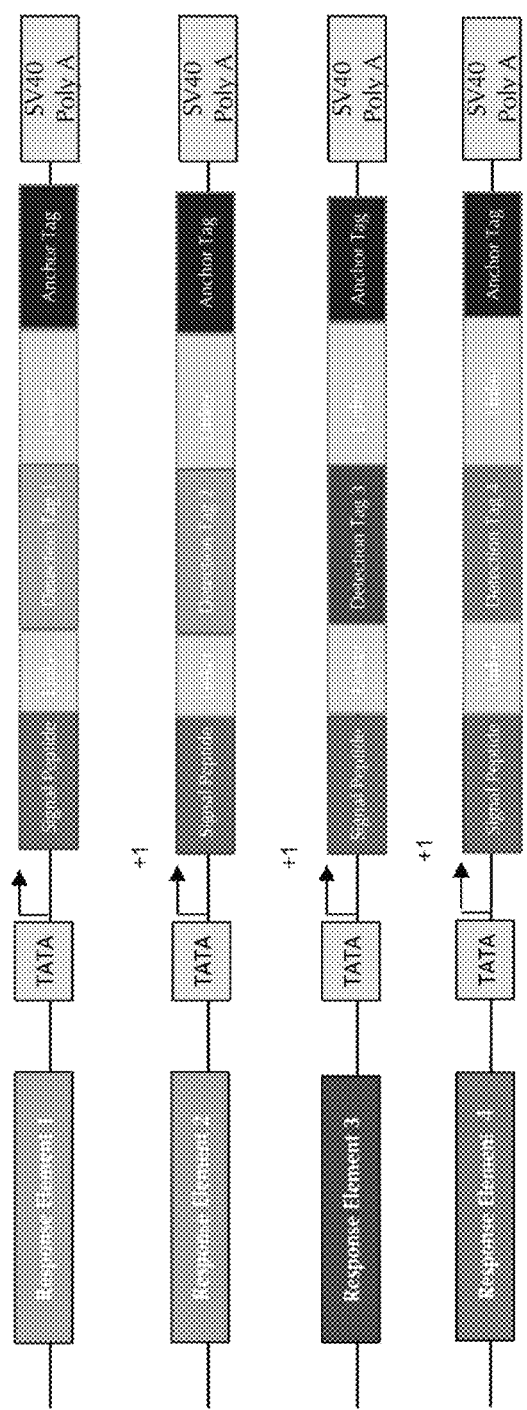

Specification includes a Sequence Listing.

(56) References Cited

OTHER PUBLICATIONS

Chung et al., "Cetuximab-Induced Anaphylaxis and IgE Specific for Galactose-α-1,3-Galactose." Eng. J. Med. 2008, 358:1109-1117.
Li et al., "Thrombocytopenia caused by the development of antibodies to thrombopoietin." Blood 2001, 98:3241-3248.
Philips, "Interferon Neutralizing Antibodies in Multiple Sclerosis." Arch. Neurol. 2010, 64:386-387.
Tovey, M.G., In Detection and Quantification of antibodies to biopharmaceuticals: Practical and Applied Considerations. Editor, Michael G Tovey, John Wiley & Sons Inc; New York. pp. 1-11, 2011.
Tannous et al., "Secreted bloo reporters: Insights and applications", Biotechnology Advances, pp. 997-1003, vol. 29 (Sep. 2011).

* cited by examiner

SECRETED REPORTER-PEPTIDES FOR OPTIMIZING CELL-BASED ASSAYS FOR ANALYSIS ON IMMUNO-ASSAY PLATFORMS

CROSS-REFERENCE TO RELATED APPLICATIONS

This application is a national phase application under 35 U.S.C. § 371 of PCT International Application No. PCT/EP2018/079292, filed Oct. 25, 2018, which claims the benefit of European Application No. 17198818.1, filed Oct. 27, 2017, each of which are herein incorporated by reference.

INCORPORATION-BY-REFERENCE OF MATERIAL SUBMITTED ELECTRONICALLY

The instant application contains a Sequence Listing which has been submitted electronically in ASCII format and is hereby incorporated by reference in its entirety. Said ASCII copy, created on May 5, 2021, is named 38526-251_ST25.txt and is 5,247 bytes in size.

FIELD OF THE INVENTION

The present invention relates to a novel system and its use in methods for determining the activity of pharmacologically active molecules including small chemical entities and large protein-based biopharmaceuticals. The system according to the invention can be used to screen libraries of small chemical entities, quantify the potency of small synthetic drugs, large protein-based biopharmaceuticals, adeno associated virus (AAV) transgenes, or cellular therapy including CAR-T cells, and to quantify the neutralizing antibody response to biopharmaceuticals, AAV vectors, AAV transgenes, or cellular therapy including CAR-T cells, as well as the effector cell function of therapeutic antibodies or Fc fusion proteins using immuno-assay platforms that are readily automated. The system according to the invention may be used in a kit or a kit of parts that may be used in a diagnostic context. Importantly, the system according to the invention may be used to determine the effectiveness of a treatment based on the use of a small synthetic drug, large therapeutic protein, recombinant or naturally occurring, AAV transgene, cellular therapy including CAR-T cells, or a therapeutic antibody or Fc fusion protein, or the immune response elicited by the therapeutic protein, therapeutic antibody, AAV vector, AAV transgene, or cells used in adoptive therapy, that may be advantageous as in the case of the induction of effector cell function or disadvantageous as in the case of a break in immune tolerance and the production of anti-drug antibodies.

BACKGROUND OF THE INVENTION

Cell-based assays are required for the detection and quantification the activity of pharmacologically active substances whether small chemical entities or large protein based biopharmaceuticals. Thus, cell-based assays are used in drug-discovery, potency assays, the assessment of neutralizing antibodies against protein-based biopharmaceuticals and antibody mediated effector functions including complement-dependent cytotoxicity (CDC), antibody-dependent cellular phagocytosis (ADCP), and antibody-dependent cell-mediated cytotoxicity (ADCC). Repeated administration of recombinant biopharmaceuticals can lead to a break in immune tolerance (1) and the production of anti-drug antibodies (ADA). In addition to adversely affecting pharmacokinetics, pharmacodynamics, bioavailability, and efficacy, ADAs can also cause immune complex disease, allergic reactions, and in some cases severe autoimmune reactions. Certain types of ADAs may also neutralize the activity of the protein therapeutic. Neutralizing antibodies (NAbs) block the biological activity of a biopharmaceutical either by binding directly to an epitope within or close to the active site of the protein or by binding to an epitope that prevents binding of the drug to a cell surface receptor. Development of neutralizing anti-drug antibodies is of particular concern in the treatment of chronic diseases, including certain forms of cancer and autoimmune or inflammatory diseases such as multiple sclerosis or rheumatoid arthritis. ADAs can result in the failure of the patient to respond to therapy and may even prove to be life threatening in the case of NAbs that cross-react with essential non-redundant endogenous proteins such as EPO or thrombopoietin (2,3). Drug-induced immunoglobulin IgE antibodies can also cause serious anaphylactic reactions (4). ADAs can also persist for long periods after cessation of treatment, thereby limiting subsequent treatment with the same drug (5). Assessment of immunogenicity is therefore an important component of drug safety evaluation in both preclinical and clinical studies. Regulatory authorities recommend the use of a cell-based assay, that reflects as closely as possible the mode of action of the drug under study, to detect and quantify neutralizing anti-drug antibodies. Cell-based assays are, however, difficult to standardize and are not readily amenable to automation.

For example, WO 2015/108763 relates to a protein reporter system comprising at least one reporter including a response element responsive to the binding of a transcription factor, a secreted enzyme backbone and a recognition region for specific binding of an antibody. Multiplexed assays for binding, assaying and quantifying the activity of transcription factors are also described, in which the assays use protein reporters in sets, libraries or other groupings, as necessary to achieve desired quantification. The document appears to enable repeatability, accuracy, and robustness in multiplexing assays.

EP 1 862 801 relates to a reporter gene assay and specifically a method in relation thereto. Specifically, the method of the document appears to relate to contacting a cell having a vector wherein a reporter gene containing a gene encoding an epitope tag having a first epitope and a second epitopes is ligated downstream to a recognition sequence of a transcription factor and a nucleotide sequence necessary for transcriptional initiation, with a test substance, a detection antibody recognizing the first epitope and an antibody recognizing the second epitope; detecting a phenomenon caused by both the detection antibodies binding to the first and second epitopes and coming close to each other; and correlating the detected phenomenon with the effect of the test substance on transcriptional regulatory mechanism, wherein the first epitope and the second epitope are arranged such that upon binding of their recognizing detection antibodies thereto, both the detection antibodies can come close to each other. The document appears to allow for measuring transcriptional activity more easily, rapidly and more accurately (i.e. with higher precision and less interference).

Tannous, B. A., et al., Biotech. Adv. 2011, 29, pp. 997-1003, relates to the use of secreted reporters detected in body fluids, which apparently are simple and useful tools in ex vivo real-time monitoring of in vivo biological processes. According to the document, cell lysis appears to be necessary for detection.

Screening libraries of chemical entities, potency assays in both drug development and manufacturing, as well as immunogenicity studies often require the testing of hundreds or thousands of individual samples necessitating the use of automated assays. The Applicant has described previously an invention that permits cell-based reporter-gene assays, including luciferase reporter-gene assays, to be analyzed on immuno-assay platforms such as Meso Scale Discovery electro-chemiluminescence (MSD-ECL), Luminex, SMC, Alpco, AlphaLISA, Gyros, or SPR Biacore without the need to re-engineer either the reporter-gene cell lines or modify the instrument, for use in either drug discovery, the quantification of the potency of biopharmaceuticals in chemistry and manufacturing control (CMC), the detection of neutralizing anti-drug antibodies or the quantification of immune mediated effector cell function such as CDC, ADCC, or ADCP (EP17165502), which is incorporated herein by reference in its entirety.

Nevertheless, there is always a desire to further improve the ease of use and performance of cell-based assays. It would be desirable to have an assay that would allow simultaneous analysis of multiple analytes, that would allow multiple sampling from a single cell culture, and that would obviate the necessity to lyse cells and remove cell debris by centrifugation prior to analysis on an automated immuno-detection platform, in addition to an increased dynamic range, improved sensitivity, and reduced costs relative to the use of cell-based reporter-gene assays.

Consequently, present invention provides at least one of the following technical advantages:
i) simultaneous analysis of multiple analytes allowing multiple sampling from a single cell culture, obviating the necessity to lyse cells and remove cell debris by centrifugation prior to analysis on an automated immuno-detection platform,
ii) increased dynamic range,
iii) improved sensitivity,
iv) reduced costs relative to the use of cell-based reporter-gene assays.

In one aspect, present invention relates to solving the problem of the provision an assay which is capable of offering
i) simultaneous analysis of multiple analytes allowing multiple sampling from a single cell culture, obviating the necessity to lyse cells and remove cell debris by centrifugation prior to analysis on an automated immuno-detection platform,
ii) increased dynamic range, and
iii) improved sensitivity.

FIGURES

FIG. 1. Model secreted reporter peptides.

The figure illustrates a series of model secreted reporter-peptides comprising a response element upstream of a TATA box operationally linked to a signal peptide and each carrying a recognition sequence, that is specific to each individual peptide, an anchor sequence, that be common to each reporter-peptide or may differ from one peptide to another, and a poly-A sequence.

Figure 2A:
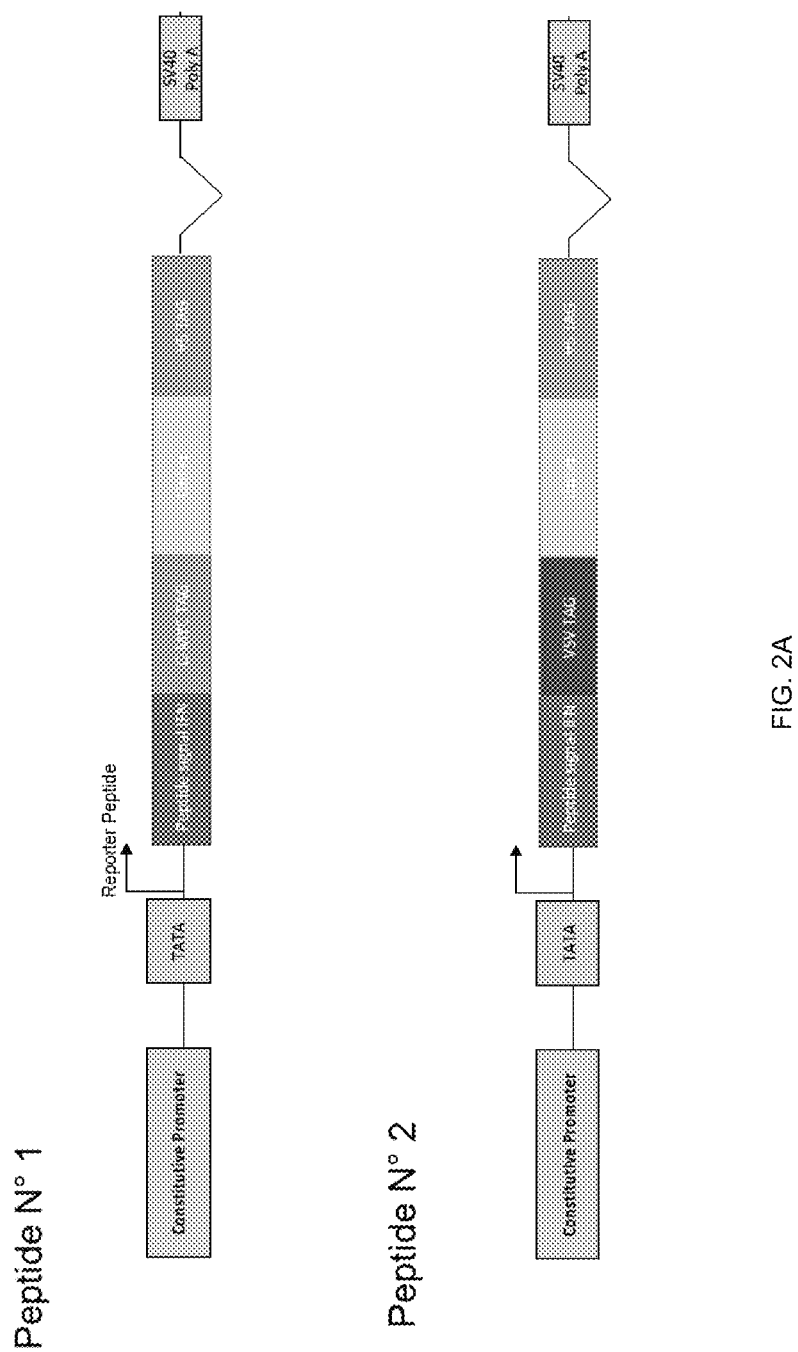

FIG. 2A. Model secreted reporter peptides.

The figure illustrates two model secreted reporter peptides according to the invention each under the control of a CMV constitutive promoter and each carrying a signal peptide derived from the gene encoding interferon alpha 2, operationally linked to a recognition sequence that is specific to each one of the two peptides. Peptide N° 1 encoded by SEQ ID NO.: 1 contains a c-Myc recognition sequence and Peptide N° 2 encoded by SEQ ID NO.: 2 carries a recognition sequence derived from the G capsid protein of vesicular stomatitis virus (VSV). The recognition sequence is operationally linked to an anchor peptide derived from the V5 protein of Blue Tongue Virus (anchor tag) and a poly-A tail. The antibody against the anchor peptide is biotin labelled such that it will attach to a streptavidin coated ELISA plate. The detection peptides are labelled with horseradish peroxidase (HRP) for detection in an ELISA.

Figure 2B:
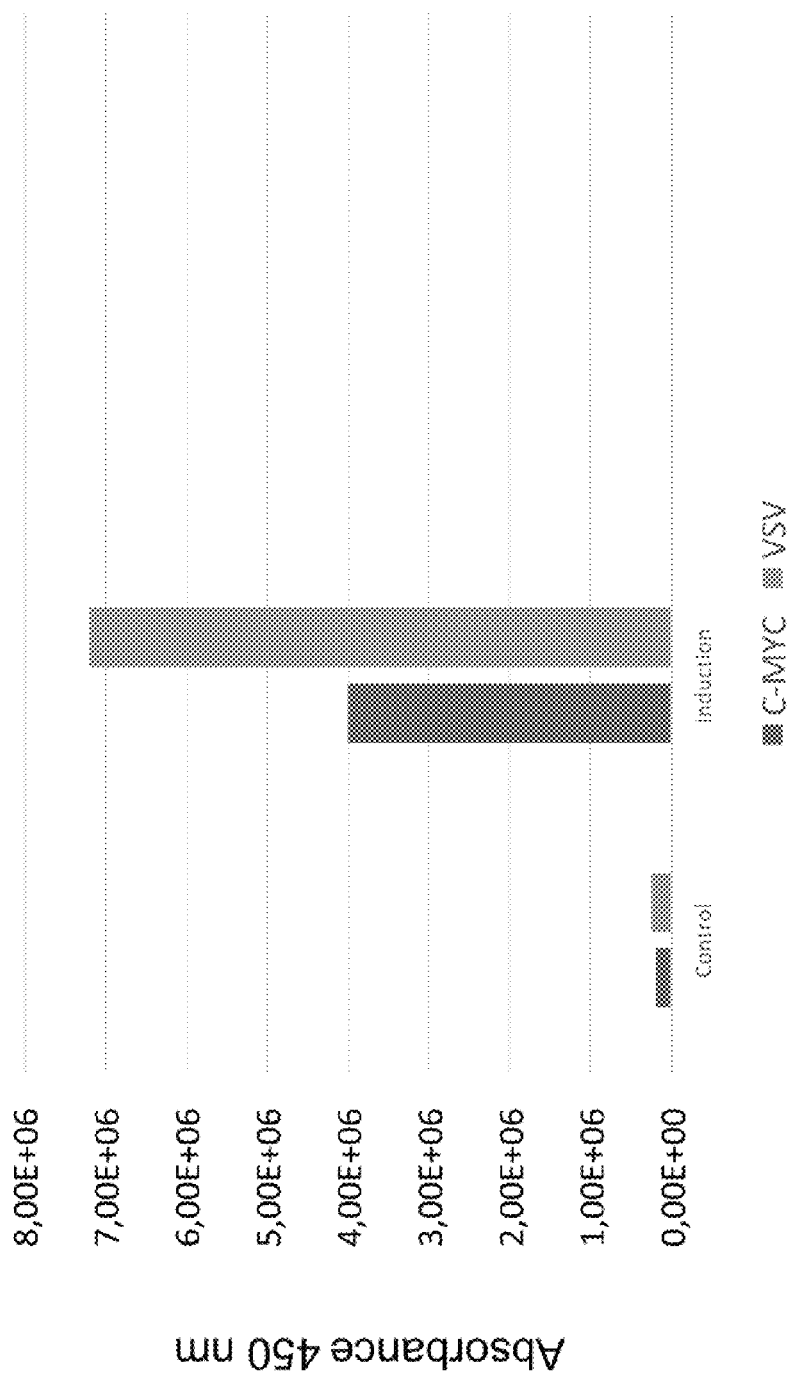

FIG. 2B. Analysis of the expression of the model reporter peptides HEK293 cells were transiently transfected with the two peptides shown in FIG. 2A and encoded by SEQ ID NO.: 1 and SEQ ID NO.: 2. The cell supernatants were harvested 18 hours later and the expression of the two peptides was quantified in a bridging ELISA using a biotin-labelled antibody specific for the V5 anchor sequence and HRP-labelled detection antibodies specific for either c-MYC or the VSV G protein.

Figure 3:
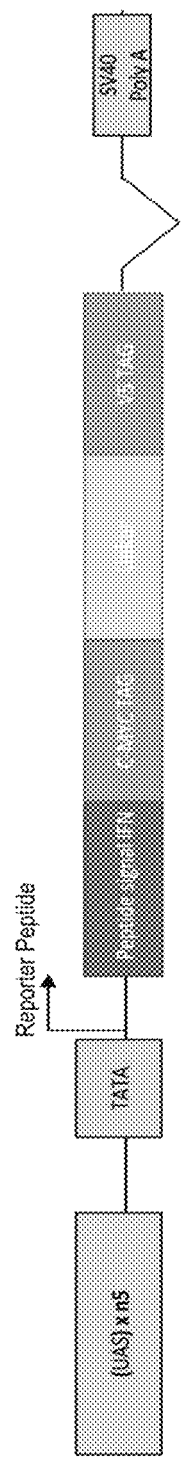

FIG. 3. A secreted reporter-peptide under the control of a chimeric promoter

The figure illustrates a reporter peptide according to the invention under the control of a cis-acting chimeric regulatory sequence consisting of a 5-fold tandem repeat of the gal4 upstream activation sequence (UAS) and a TATA box operationally linked to the signal peptide derived from the gene encoding interferon alpha 2, a c-Myc recognition sequence, a peptide derived from the V5 protein of Blue Tongue Virus (anchor tag), and a poly-A tail encoded by (Sequence ID 3).

Figure 4:
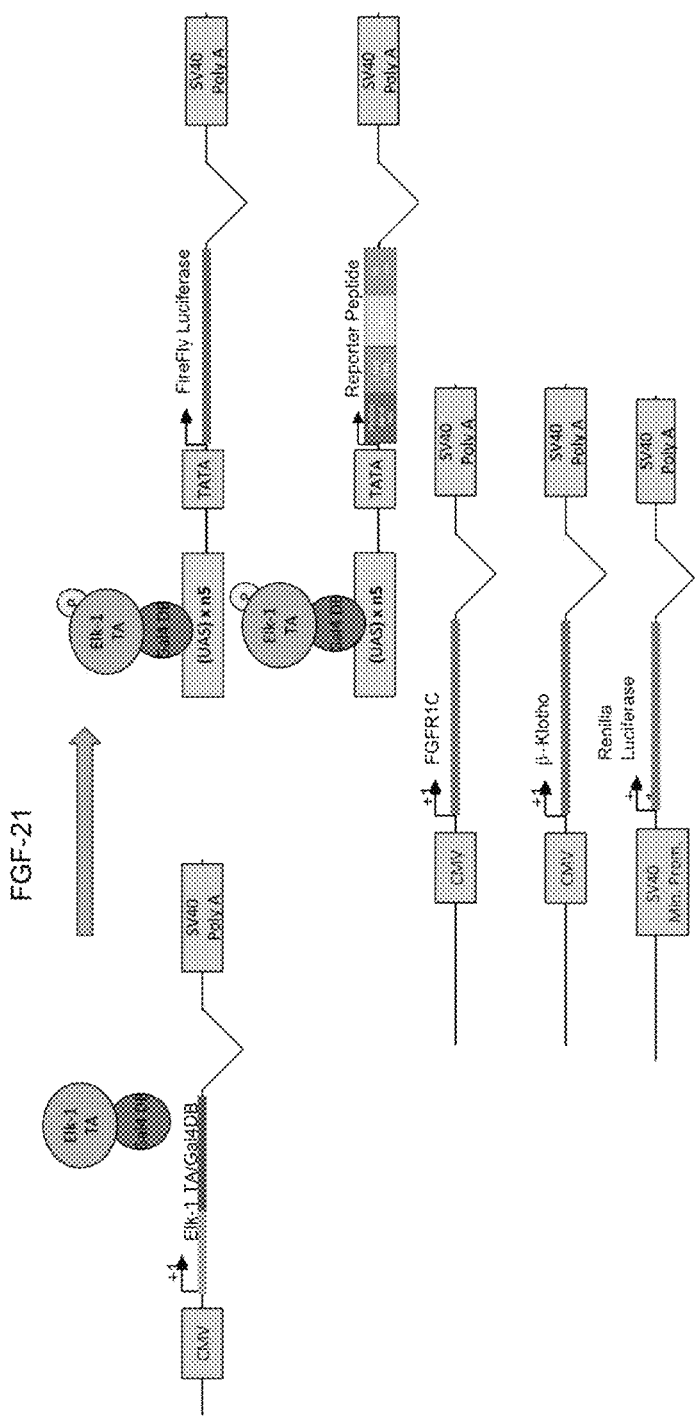

FIG. 4. Quantification of FGF-21 activity using a secreted reporter-peptide. HEK293 cells were co-transfected with a secreted reporter-peptide according to the invention encoded by SEQ ID NO.: 3 and described in the legend of FIG. 3, and an expression vector for a chimeric transcription factor comprising the trans-activation domain of Elk-1 fused to a synthetic DNA binding domain absent in animal cells and capable of binding to the gal4 UAS cis-acting regulatory sequence of the reporter peptide, and expression vectors for a cell surface bound heterodimeric receptor protein comprising the tyrosine kinase FGFR1c receptor chain and a beta-Klotho co-receptor protein together with the Renilla luciferase normalization gene. A stable clonal cell line was isolated and characterized for FGF-21 responsiveness. The recombinant cells containing the secreted reporter-peptide were treated with FGF-21 and the cell supernatants were harvested 18 hours later and the expression of the peptide was quantified in a bridging ELISA using a biotin-labelled attachment antibody specific for the V5 anchor sequence attached to a streptavidin-coated microtiter assay plate and HRP-labelled detection antibody specific for c-Myc.

Figure 5:
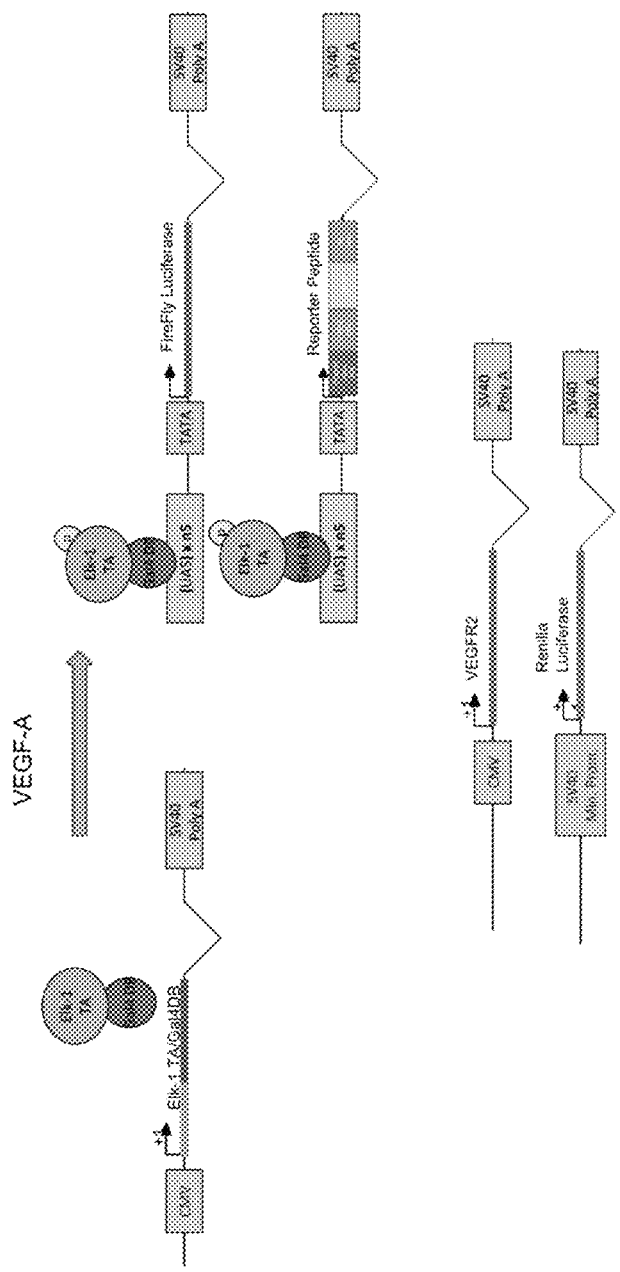

FIG. 5. Quantification of VEGF activity using a secreted reporter-peptide. HEK293 cells were co-transfected with a secreted reporter-peptide according to the invention encoded by SEQ ID NO.: 3 and described in the legend of FIG. 3, and an expression vector for a chimeric transcription factor comprising the trans-activation domain of Elk-1 fused to a synthetic DNA binding domain absent in animal cells and capable of binding to the gal4 UAS cis-acting regulatory sequence of the secreted reporter peptide, and an expression vector for the cell surface bound VEGFR2 receptor protein together with the Renilla luciferase normalization gene. A stable clonal cell line was isolated and characterized for VEGF responsiveness. The recombinant cells containing the secreted reporter-peptide were treated with VEGF and the supernatants harvested 18 hours later and the expression of the reporter-peptide was quantified in a bridging ELISA using a biotin-labelled attachment antibody specific for the V5 anchor sequence attached to streptavidin-coated assay plates and HRP-labelled detection antibody specific for c-Myc.

Figure 6A:
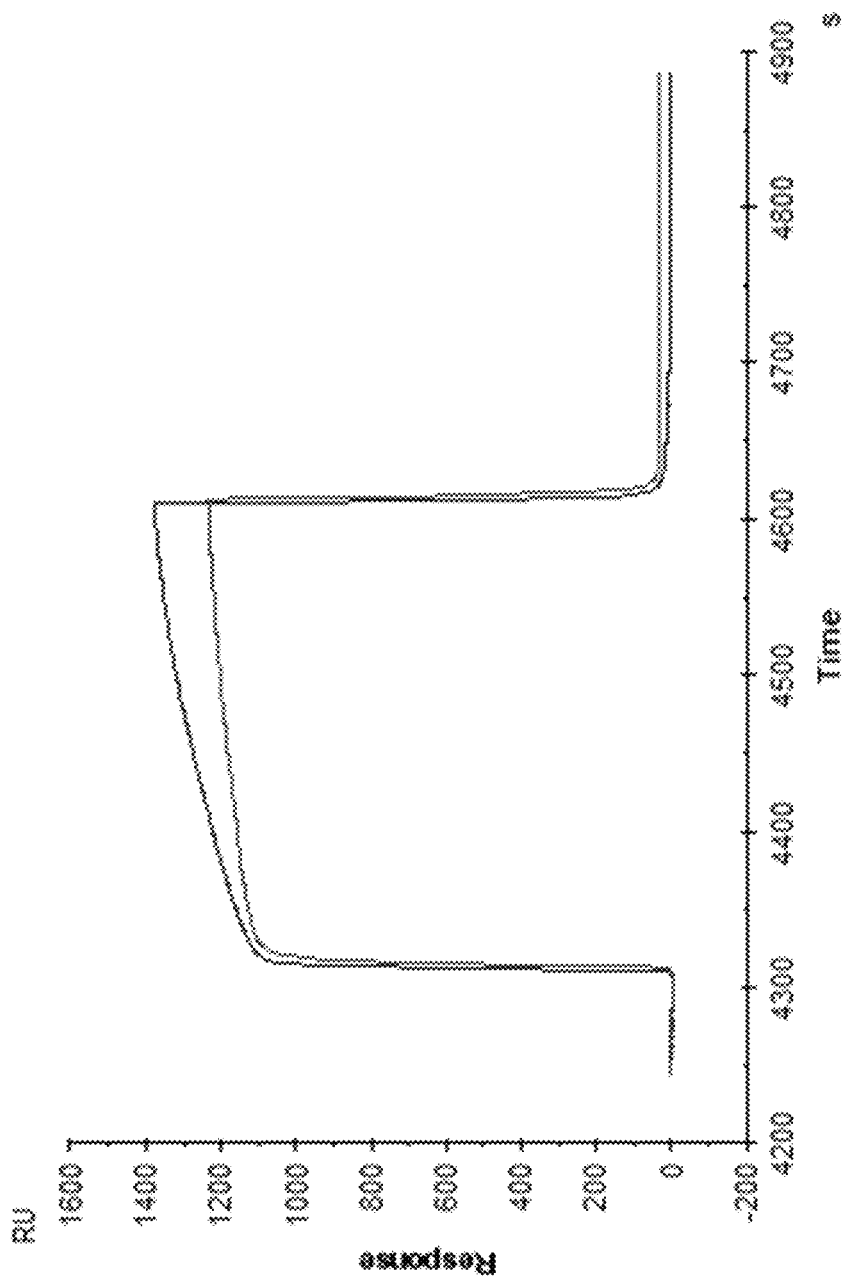

FIG. 6A. Biacore sensogram demonstrating label-free detection of a reporter-peptide.

HEK293 cells were transiently transfected with peptide N° 1 encoded by SEQ ID NO.: 1 and illustrated in FIG. 2A. The cell supernatants were harvested 18 hours later and the expression of the reporter-peptide was quantified using a biotin-labelled attachment antibody, specific for the V5 anchor sequence, immobilized on a streptavidin coated gold sensor surface in a Biacore 3000 SPR instrument following injection of the cell supernatants containing the reporter peptide.

Figure 6B:
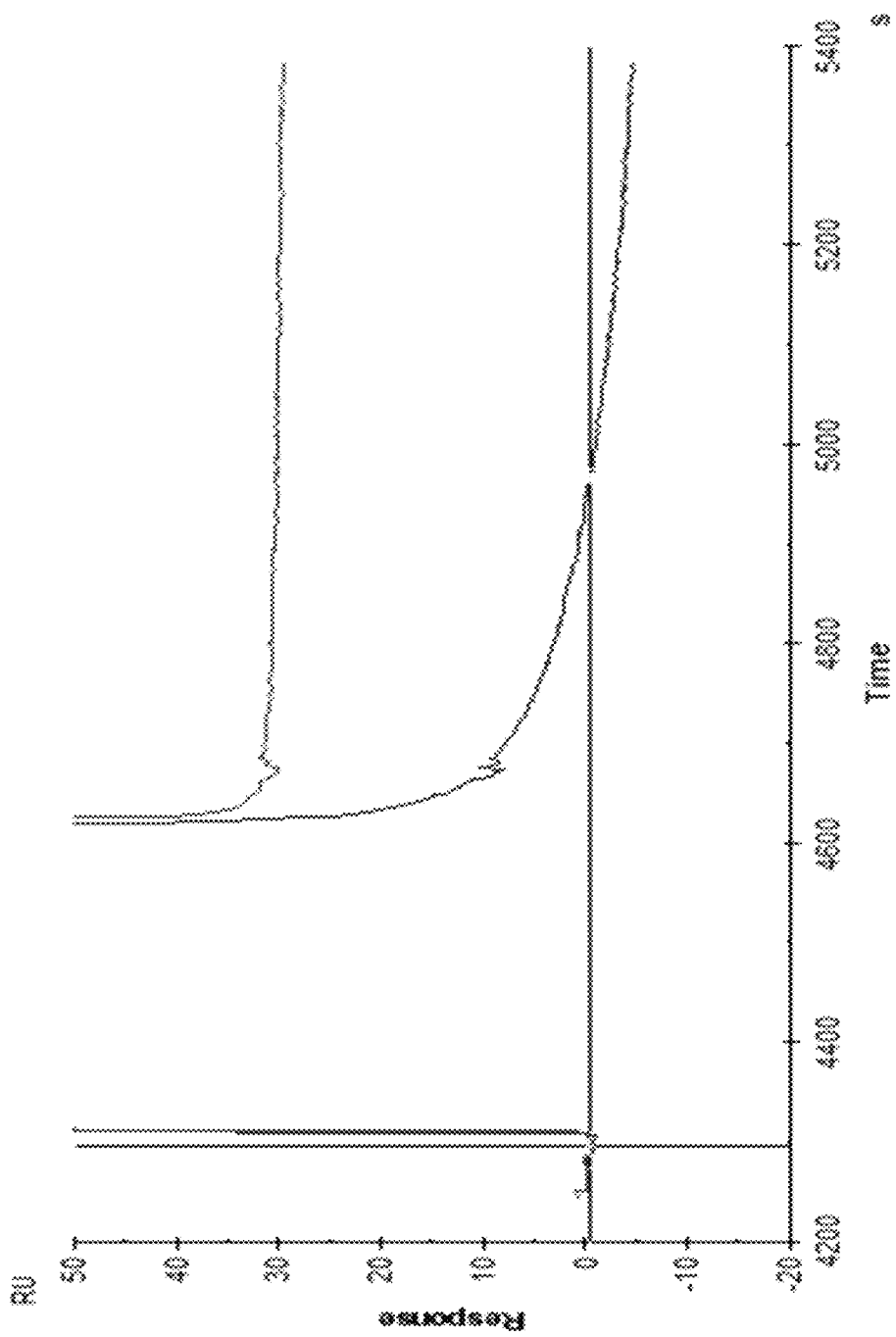

FIG. 6B. Expanded scale of the Biacore sensogram demonstrating label-free detection of a reporter-peptide.

The scale of part of the Biacore sonsogram shown in FIG. 5A was expanded to show more clearly the specific binding of the reporter-peptide N° 1 to the biotin-labelled anti-V5 antibody anchor antibody attached to the streptavidin coated gold sensor surface.

SUMMARY OF THE INVENTION

The present invention solves the above mentioned problems and provides i.a. a substantial improvement of cell-based assays for analysis using immuno-detection platforms that can be readily automated and allows simultaneous analysis of multiple analytes, multiple sampling from a single cell culture, and obviates the necessity to lyse cells and remove cell debris by centrifugation prior to analysis on an automated immuno-detection platform. The present invention also provides a means of increasing the dynamic range, sensitivity, and reducing the cost of cell-based assays.

Consequently, the present invention relates to small secreted reporter-peptides 15 to 150 amino-acids in length comprising a response element activated by one or more transcription factors, induced by the pharmacology active substance to be analyzed following its interaction with a specific intracellular or cell surface molecule. Immediately down-stream of the response element of the reporter peptide is a TATA box allowing efficient transcription of the peptide within a cell, a signal peptide, that ensures efficient secretion of the peptide when expressed within a cell, together with anchor and detection sequences to which antibodies can be raised, the later three elements functionally attached to a polyadenylation sequence (poy-A tail) to ensure efficient translation within a cell. The anchor sequence (Anchor Tag) may differ from one peptide to another or may be common to multiple reporter-peptides such that all the peptides can be detected simultaneously by ELISA, or by the use of a commonly available immuno-detection platform such as MSD, Gyros, AlphaLisa, or Biacore. In an additional embodiment of the invention the anchor sequence encodes streptavidin binding protein allowing the peptide to attach directly to a streptavidin coated micro-titer plate or other streptavidin-coated surface, eliminating the requirement for an antibody to be raised against the anchor sequence. The detection sequence (Detection Tag) differs from one peptide to another such that each peptide can be detected simultaneously using antibodies specific for each detection sequence. Each detection antibody is labelled in such a manner that it can be detected using one of the commonly available immuno-detection platforms. Thus, the antibodies directed against each one of the detection sequences are labelled on their Fc moieties with for example a Sulfo-Tag that permits detection of the peptide on the MSD platform, or Alexa that permits detection on the Gyros platform, or digoxigenin that permits detection of on the PerkinElmer AlphaLISA platform. In the case of SPR using the Biacore system no detection antibody is required.

The invention also relates to a cell. In particular, the invention relates to a cell comprising the reporter-peptide according to the invention. The cell may be of any origin and in particular, a mammalian or avian cell. Importantly, the cell may further express a second or multiple reporter-peptides comprising different regulatory and recognition sequences. The cells according to the invention may be of any origin including animal or avian and can be primary cells naturally occurring or recombinant such as e.g. CAR-T cells, or any cell line known in the art such as e.g. Jurkat, Raji, HEK293, KHYG-1, DT-40 cells, or MSB-1.

The invention also relates to a kit or a kit of parts. The kit may comprise:
   i) a cell according to the invention;
   ; and
   ii) an antibody directed against the anchor sequence that
      may be biotinylated or not
   ; and
   iii) an antibody directed against the detection sequence
      that be labelled or not with a Sulfo-Tag that permits
      detection of the peptide on the MSD platform, or Alexa
      that permits detection on the Gyros platform, or digoxigenin that permits detection of on the PerkinElmer AlphaLISA platform or left unlabeled for detection by SPR using the Biacore platform or other SPR platforms.
   ; and
   iv) a streptavidin coated microtiter plate or other streptavidin-coated surface such as a SPR chip.

The kit may also comprise one or more vials, such as e.g. 2 or more vials etc of assay-ready frozen cells.

In one aspect the invention relates to peptides as disclosed herein where the peptides act as either the signal peptide and/or the anchor.

In a further aspect of the invention, the signal peptide and the anchor are different. In a further aspect the signal peptide and/or the anchor peptide may be according to the sequences as disclosed herein. In yet a further aspect, the signal peptide and/or the anchor peptide be according to the sequences as disclosed herein, with the proviso that the sequences are different. Thus, according to the invention, the detection peptide and/or the anchor as mentioned above may be selected from any one of SEQ ID NO.: 4-7.

As mentioned above, in one aspect, the detection peptide is different from the anchor peptide. Thus, the signal peptide may be selected from any one of SEQ ID NO.: 4-7, and whereas the anchor peptide may be selected from any one of SEQ ID NO.: 4-7 with the proviso that the signal peptide is different from the anchor peptide.

In one aspect the detection and/or the anchor peptide may be any peptide sequence comprising a sequence identity of at least 70% to SEQ ID NO.: 4, such as e.g. at least 75%, e.g. at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 4.

In one aspect the detection and/or the anchor peptide may be any peptide sequence comprising a sequence identity of at least 70% to SEQ ID NO.: 5, such as e.g. at least 75%, e.g.

at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 5.

In one aspect the detection and/or the anchor peptide may be any peptide sequence comprising a sequence identity of at least 70% to SEQ ID NO.: 6, such as e.g. at least 75%, e.g. at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 6.

In one aspect the detection and/or the anchor peptide may be any peptide sequence comprising a sequence identity of at least 70% to SEQ ID NO.: 7, such as e.g. at least 75%, e.g. at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 7.

The invention also relates to a polynucleotide.

In one aspect, the invention relates to a polynucleotide which may be any one of sequences SEQ ID NO.: 1-3.

In one aspect the polynucleotide may be any DNA sequence comprising a sequence identity of at least 70% to SEQ ID NO.: 1, such as e.g. at least 75%, e.g. at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 1.

In one aspect the polynucleotide may be any DNA sequence comprising a sequence identity of at least 70% to SEQ ID NO.: 2, such as e.g. at least 75%, e.g. at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 2.

In one aspect the polynucleotide may be any DNA sequence comprising a sequence identity of at least 70% to SEQ ID NO.: 3, such as e.g. at least 75%, e.g. at least 80%, e.g. at least 85%, e.g. at least 90%, e.g. at least 95%, e.g. at least 96%, e.g. at least 97%, e.g. at least 98%, e.g. at least 99%, or a sequence comprising the identical sequence to SEQ ID NO.: 3.

The invention also relates to a method for quantifying the activity of a drug, a small molecule, large biopharmaceutical, AAV transgene, cellular therapy, or the antibody response to a protein-based drug, AAV vector, AAV transgene, or cellular therapy, or the effector cell function of a therapeutic antibody, Fc fusion protein, or cellular therapy ex vivo in clinical samples from patients treated with a therapeutic.

The method may comprise the steps of;
a) contacting a sample obtained from a patient undergoing treatment with cells according to the invention.
b) harvesting the culture supernatant from the cells according to the invention
c) analyzing the sample by ELISA or on a commonly available immuno-analysis platform.

The term reporter peptide as used herein is intended to comprise one or more of a response element (or upstream activation sequence), a TATA box, a signal peptide, an anchor tag and a detection tag.

The term polyadenylation sequence (Poly A) as used herein is intended to mean any sequence right in adenine which is required to ensure efficient translation of the peptide within a cell but is generic and is not part of the translated peptide. The poly A sequence may be from SV40 or other poly A sequences, such as e.g. from hGH, BGH, or rbGlob.

DETAILED DESCRIPTION OF THE INVENTION

The present invention relates to small secreted reporter-peptides devoid of enzymatic activity and hence when expressed within a cell are less influenced by culture conditions and other external factors and are not influenced by differences in the activity of a substrate in contrast to conventional reporter-genes such as luciferase reporter genes other enzyme detection systems such as chloramphenicol acetyl transferase, β-galactosidase, or alkaline phosphatase. The present invention relates to small secreted reporter-peptides 15 to 150 amino-acids in length comprising a response element activated by one or more transcription factors, induced by the pharmacology active substance to be analyzed following its interaction with a specific intracellular or cell surface molecule, operationally linked to a TATA box allowing efficient transcription of the peptide within a cell, a signal peptide, that ensures efficient secretion of the peptide when expressed within a cell, anchor and detection sequences to which antibodies can be raised, and a polyadenylation sequence ensuring efficient translation within a cell. The anchor sequence encodes a peptide that does not cross-react with a cellular protein and for which antibodies are available commercially such as the V5 protein from the blue tongue virus or may encode a novel proprietary peptide with minimal sequence homology with cellular proteins and that is predicted to be immunogenic allowing antibodies to be raised against the peptide such as those shown in Sequence ID 4 to 7. The detection sequence encodes either a peptide such as the VSV G capsid protein or the c-Myc proto-oncogene for which antibodies are readily available commercially or a novel proprietary peptide with minimal sequence homology with cellular proteins and that is predicted to be immunogenic allowing antibodies to be raised against the peptide such as those shown in Sequence ID 4 to 7. The sequences shown in Sequence ID 4 to 7 may be used as either an anchor sequence or a detection sequence.

Moreover, and as is apparent from the above, the reporter peptide comprises sequences relating to both the detection and anchor sequences as mentioned above. In one aspect, the detection and anchor sequences are different and may be interchangeable, i.e. antibodies directed against one sequence can be used as either the anchor or detection antibody.

The anchor sequence (Anchor Tag) may differ from one peptide to another or may be common such that all the peptides can be detected simultaneously by ELISA, or by the use of one of the commonly available immuno-detection platforms such MSD, Gyros, AlphaLisa, or Biacore. The Gyros platform technology is based on the use of centrifugal control of capillary action using a CD engineered to incorporate nanoliter microfluidics and a detection system based on laser activated fluorescence. Immunogenicity assays using the Gyros platform are based on a bridging ELISA in which anti-drug antibodies are detected by the formation of a bridge between two molecules of the drug consisting of one molecule of a therapeutic antibody (monoclonal or polyclonal) labelled with biotin and another molecule of a therapeutic antibody (monoclonal or polyclonal) labelled with a florescent marker such as Alexa. The presence of anti-drug antibodies in a sample will form a bridge allowing the Alexa labelled drug molecule to be bound to the biotin labelled drug molecule that it is turn bound to a streptavidin coated bead. The fluorescence emitted by the Alexa labelled bound drug is then quantified following activation with a laser. Alternatively, the potency of a therapeutic antibody may be quantified using an anti-drug antibody pair, specific for the therapeutic antibody, labelled with biotin and Alexa that detects the drug that forms a bridge between the two anti-drug antibodies molecules (monoclonal or polyclonal). A different dual labelled drug pair is required for each Gyros ADA assay. In contrast, according to the present invention a single common anchor sequence can be used for multiple reporter-peptides for the detection of different analytes allowing a single capture antibody, monoclonal or polyclonal, to be used to anchor all the reporter-peptides. In an additional embodiment of the invention the anchor sequence encodes streptavidin binding protein allowing the peptide to attach directly to the streptavidin coated Gyros beads eliminating the requirement for an antibody to be raised against the anchor sequence. The antibodies directed against each one of the detection sequences are labelled on their Fc moieties with Alexa that permits detection of multiple analytes on the Gyros platform by using different wells of the PCR loading plate.

The MSD platform technology is based on the use of electrochemiluminescence and a detection system based on a Sulfo-Tag labelled antibody that detects an analyte bound to a capture antibody that is in turn bound to a carbon or gold coated 96-well plate with an embedded electrode. Immunogenicity assays using the MSD platform are based on a bridging ELISA in which anti-drug antibodies are detected by the formation of a bridge between two molecules of the drug, one molecule of which is labelled with biotin and bound to a streptavidin-coated gold plate and another molecule of the drug that is labelled with a Sulfo-Tag. The presence of anti-drug antibodies in a sample will form a bridge allowing the Sulfo-Tag labelled drug molecule to be bound to the biotin labelled drug molecule that it is turn bound to a streptavidin-coated plate. The light signal emitted by the Sulfo-Tag labelled bound drug is then quantified. Alternatively, the potency of a therapeutic antibody may be quantified using an anti-drug antibody pair, specific for the therapeutic antibody, labelled with biotin and the Sulfo-Tag that detects the drug that forms a bridge between the two anti-drug antibodies molecules (monoclonal or polyclonal). A different dual labelled drug pair is required for each MSD ADA assay. In contrast, according to the present invention a single common anchor sequence can be used for multiple reporter-peptides for the detection of different analytes such that a single antibody, monoclonal or polyclonal, can be used for all the secreted reporter-peptides. In an additional embodiment of the invention the anchor sequence encodes streptavidin binding protein allowing the peptide to attach directly to the streptavidin coated MSD plate eliminating the requirement for an antibody to be raised against the anchor sequence. The antibodies directed against each one of the detection sequences are labelled on their Fc moieties with a Sulfo-Tag that permits detection of multiple analytes on the MSD platform by using different wells of the MSD assay plate.

The PerkinElmer AlphaLISA solution ELISA platform technology is based on the use of streptavidin coated donor beads and a detection system based on digoxigenin-labelled acceptor beads in which an ADA forms a bridge between a biotin labelled drug attached to the streptavidin coated donor beads and the digoxigenin-labelled acceptor beads. The labelled drug ADA complexes are detected using anti-digoxigenin-HRP conjugate and quantification of the luminescence signal. A different dual labelled drug pair is required for each AlphaLISA ADA assay. In contrast, according to the present invention a single common anchor sequence can be used for multiple secreted reporter-peptides for the detection of different analytes such that a single antibody, monoclonal or polyclonal, can be used for all the secreted reporter-peptides. In an additional embodiment of the invention the anchor sequence encodes streptavidin binding protein allowing the peptide to attach directly to the streptavidin coated donor beads eliminating the requirement for an antibody to be raised against the anchor sequence. The antibodies directed against each one of the detection sequences are labelled on their Fc moieties with a digoxigenin-HRP that permits detection of multiple analytes on the AlphaLISA platform.

The Biacore platform is based on the use of surface plasmon resonance (SPR) that allows real-time, label-free detection of biomolecular interactions. A biotin labelled anchor antibody is immobilized on a streptavidin-coated gold sensor surface in the Biacore instrument and a sample containing the supernatant from cells transfected with the secreted reporter-peptide is injected over the surface. Polarized light is then directed at the sensor surface and the angle of minimum intensity reflected light is detected. This generates electron charge density waves called plasmons, reducing the intensity of reflected light at a specific angle known as the resonance angle, in proportion to the mass on a sensor surface. This angle changes as molecules bind and dissociate and the interaction profile is thus recorded in real time in a sensorgram. The results of the experiments illustrated in Example 4 show that expression of the reporter-peptides can be readily quantified using the Biacore label-free detection system.

In an additional embodiment of the invention pre-existing reporter-gene cell lines such as those containing a luciferase reporter-gene, can be co-transfected with one or more of the reporter-peptides without interference from the pre-existing reporter-gene. This obviates the necessity to re-engineer pre-existing reporter gene cell lines in particular those containing multiple molecular constructs such as the reporter-gene cell lines described in Examples 3 & 4.

In an additional embodiment of the present invention a cell may be transfected with multiple reporter-peptides each containing different response elements and detection sequences, and the same or different anchor sequences, thus allowing multiple pharmacologically active substances to be detected simultaneously and allowing biological activity to be analyzed in an automated manner using commonly available immuno-detection platforms. Said secreted reporter-peptides can also be used to determine the interaction between different pharmacologically active substances used in combination therapy. In addition, said secreted reporter-peptides can also be used to quantify the effector cell function of therapeutic antibodies or Fc fusion proteins including antibody dependent cellular cytotoxicity (ADCC), antibody dependent cellular phagocytosis (ADCP), and complement dependent cytotoxicity (CDC) in the presence of suitable target cells in an automated manner using commonly available immuno-detection platforms. Said peptides can also be used to quantify the potency and neutralizing antibody response to adeno associated virus (AAV) vectors and to one or more specific AAV transgenes in an automated manner using commonly available immuno-detection platforms.

The invention also relates to a cell. In particular, the invention relates to a cell comprising the secreted reporter-peptide according to the invention. The cell may be of any origin and either a primary cell such as a T or B lymphocyte, a monocyte or natural killer cell or a genetically modified primary cell such as a CAR-T cell and in particular, a human, animal, or avian cell. Importantly, the cell may further express a second or multiple reporter-peptides comprising different regulatory and recognition sequences. The cells according to the invention may also be of any cell line known in the art such as e.g. the human cell lines, Jurkat, Raji, HEK293, KHYG1, or the murine cell line RAW264.7 or an avian cell line such as DT-40 or MSB-1.

In a further aspect, present invention relates to use of the cells according to present invention in an assay, wherein the assay may be an automated assay or any other automated diagnostic setting.

The invention also relates to a kit or a kit of parts. The kit may comprise:
  i) a cell according to the invention;
  ; and
  ii) an antibody directed against the anchor sequence that may be biotinylated or not
  ; and
  iii) an antibody directed against the detection sequence that be labelled or not with a Sulfo-Tag that permits detection of the peptide on the MSD platform, or Alexa that permits detection on the Gyros platform, or digoxigenin that permits detection of on the PerkinElmer AlphaLISA platform, or left unlabeled for detection by SPR on a Biacore platform.
  ; and
  iv) a streptavidin-coated microtiter plate or streptavidin-coated beads, or a streptavidin-coated SPR chip.

The kit may also comprise one or more vials, such as e.g. 2 or more vials etc of assay-ready frozen cells.

The invention also relates to a method for quantifying the activity of a drug, whether a small molecule, large biopharmaceutical, AAV transgene, or cellular therapy such as a CAR-T cell; or the antibody response to a protein-based drug, or AAV viral vector or AAV transgene, or cellular therapy such as a CAR-T cell; or the effector cell function of a therapeutic antibody or Fc fusion protein, or cellular therapy ex vivo in clinical samples from patients treated with a therapeutic antibody, Fc fusion protein, or cellular therapy.

The method may comprise the steps of;
  a) contacting a sample obtained from a patient undergoing treatment with cells according to the invention.
  b) harvesting the supernatant after an appropriate period of time
  c) addition of the anchor & detection antibodies
  d) analysis of the sample by ELISA or on the appropriate immuno-assay platform.

In summary, present invention relates to small secreted reporter-peptides 15 to 150 amino-acids in length comprising a response element, activated by one or more transcription factors induced by the pharmacology active substance to be analyzed following its interaction with a specific intracellular or cell surface molecule, functionally linked to a response element, a TATA box, a signal peptide, anchor and detection sequences to which antibodies can be raised, and a poy-A tail. The anchor sequence may differ from one peptide to another or may be common to multiple secreted reporter-peptides such that all the peptides can be analyzed simultaneously by ELISA, or by the use of a commonly available immuno-detection platform such MSD, Gyros, AlphaLisa, or Biacore. The detection sequence is unique to each secreted reporter-peptide and may be labelled with a Sulfo-Tag that permits detection of the peptide on the MSD platform, or Alexa that permits detection on the Gyros platform, or digoxigenin that permits detection of on the PerkinElmer AlphaLISA platform, or left unlabeled for detection by SPR on a Biacore platform. The present invention provides i.a. a substantial improvement of cell-based assays for analysis using automated immune-detection platforms and allows simultaneous analysis of multiple analytes, multiple sampling from a single cell culture, and obviates the necessity to lyse cells and remove cell debris by centrifugation prior to analysis on an automated immuno-detection platform. The present invention also provides a means of increasing the dynamic range, sensitivity and reducing the cost of cell-based assays and can be applied to existing engineered cell lines, such as those containing a reporter-gene such as a luciferase reporter-gene obviating the requirement for a luciferase substrate to quantify luciferase activity and the necessity to extensively re-engineer cell lines containing multiple molecular constructs.

EXAMPLES

Example 1

HEK293 cells were co-transfected with the two secreted reporter-peptides shown in FIG. 2A. Each peptide is under the control of a constitutive promoter and carries an interferon alpha 2 signal peptide. Each peptide also carries a peptide derived from the V5 protein of Blue Tongue Virus (anchor tag) and a recognition sequence that is specific for one or the other of the two peptides. Peptide N° 1 encoded by SEQ ID NO.: 1 contains a c-Myc recognition sequence and Peptide N° 2 encoded by SEQ ID NO.: 2 carries a recognition sequence derived from the G capsid protein of vesicular stomatitis virus (VSV). The antibody against the anchor peptide is biotin labelled such that it will attach to a streptavidin coated ELISA plate. The antibodies directed against the detection peptides are labelled with horseradish peroxidase (HRP). The culture supernatants were collected 18 hours after transient transfection of HEK293 cells with both peptides and analyzed using a bridging ELISA consisting of a biotin labelled monoclonal antibody against the blue tongue V5 protein (AbCam catalogue N° ab18617) bound to a strepatavidin-coated microtiter assay plate and HRP labelled anti-c-Myc (AbCam, catalogue N° ab1261) and HRP-labelled anti-VSV G-protein (AbCam catalogue N° ab3556) detection antibodies. The results of the experiment show clearly that both reporter-peptides can be readily detected in the culture supernatant without any cross-reactivity between each peptide or with any other secreted peptide or protein (FIG. 2B).

Example 2

HEK293 cells were co-transfected with the secreted reporter-peptide according to the invention encoded by SEQ ID NO.: 3 under the control of a cis-acting chimeric regulatory sequence consisting of a 5-fold tandem repeat of the gal4 upstream activation sequence (UAS) and a TATA box operationally linked to the signal peptide derived from the gene encoding interferon alpha 2, a c-Myc recognition sequence, a peptide derived from the V5 protein of Blue Tongue Virus (anchor tag), and a poly-A tail (FIG. 3). The cells were co-transfected with an expression vector for a chimeric transcription factor comprising the trans-activation domain of Elk-1 fused to a synthetic DNA binding domain capable of binding to the gal4 UAS cis-acting regulatory sequence of the secreted reporter peptide, and expression vectors for a cell surface bound heterodimeric receptor protein comprising the tyrosine kinase FGFR1c receptor chain and a beta-Klotho co-receptor protein together with the Renilla luciferase normalization gene (FIG. 4). A stable clonal cell line was isolated and characterized for FGF-21 responsiveness. The recombinant cells containing the secreted reporter-peptide were treated with recombinant FGF-21 and the cell supernatants were harvested 18 hours later and the expression of the peptide was quantified in a bridging ELISA using a biotin-labelled attachment antibody specific for the V5 anchor sequence attached to a streptavidin-coated microtiter assay plate and a HRP-labelled detection antibody specific for c-Myc.

Example 3

HEK293 cells were co-transfected with a secreted reporter peptide according to the invention under the control of a cis-acting chimeric regulatory sequence consisting of a 5-fold tandem repeat of the gal4 upstream activation sequence (UAS) and a TATA box operationally linked to a signal peptide derived from the gene encoding interferon alpha 2, a c-Myc recognition sequence, a peptide derived from the V5 protein of Blue Tongue Virus (anchor sequence), and a poly-A tail. HEK293 cells were also co-transfected with an expression vector for a chimeric transcription factor comprising the trans-activation domain of Elk-1 fused to a synthetic DNA binding domain capable of binding to the gal4 UAS cis-acting regulatory sequence of the reporter peptide, and an expression vector for the cell surface bound VEGFR2 receptor protein together with the Renilla luciferase normalization gene (FIG. 5). A stable clonal cell line was isolated and characterized for VEGF responsiveness. The recombinant cells containing the secreted reporter-peptide were treated with recombinant VEGF and the supernatants were harvested 18 hours later and the expression of the secreted reporter-peptide was quantified in a bridging ELISA using a biotin-labelled attachment antibody specific for the V5 anchor sequence attached to streptavidin-coated assay plates and a HRP-labelled detection antibody specific for c-Myc.

Example 4

HEK293 cells were transiently transfected with the secreted reporter-peptide N° 1 encoded by SEQ ID NO.: 3 shown in FIG. 2A. The cell supernatants were harvested 18 hours later and the expression of the secreted reporter-peptide was quantified using SPR. A biotin labelled Anti-V5 antibody was immobilized on a streptavidin-coated gold sensor surface in a Biacore 3000 instrument and a sample containing the supernatant from cells transfected with the secreted reporter peptide was injected over the surface.

REFERENCES

1. Tovey, M. G., In Detection and Quantification of antibodies to biopharmaceuticals: Practical and Applied Considerations. Editor, Michael G Tovey, John Wiley & Sons Inc; New York. pp 1-11, 2011.
2. Casadevall, et al N. Eng. J. Med. 346:469-475, 2002
3. Li J. et al Blood, 98:3241-3248, 2001
4. Chung C. H. et al Eng. J. Med. 358:1109-1117, 2008
5. Philips, J. T. Arch. Neurol. 64:386-387, 2010

In Specific Embodiments the Invention Also Relates to the Following Items

1. A polynucleotide comprising a response element, to which one or more transcription factors can bind, operationally linked to a TATA box, a signal peptide, anchor and detection sequences, to which antibodies can be raised, and a polyadenylation sequence, the expression of which, in a cell that possesses an intracellular or cell surface molecule that will interact specifically with an analyte, is proportional to the activity of the analyte that can be quantified, following secretion of the reporter-peptide into the cell supernatant, and analysis using an ELISA or a commonly available immuno-detection platform;

wherein the immuno-detection platform is
   an ELISA
   MSD
   Gyros
   AlphaLISA
   SPR—Biacore
   or similar immune-detection platform 2. A cell transfected with one or more polynucleotides according to item 1 each encoding a different response element and each one activated by a different pharmacologically active analyte following the interaction of the analyte with an intracellular or cell surface molecule, and a detection sequence unique to each polypeptide;

wherein the cell according to the invention is a primary cell such as a T or B lymphocyte, a monocyte or natural killer cell of human or animal origin naturally occurring or recombinant such as a CAR-T cell, or any cell line known in the art such as e.g. human Jurkat, Raji, HEK293, KHYG1, or murine RAW264.7, or an avian cell line such as DT-40 or MSB-1, or a previously established engineered cell line such as a cell line containing a reporter-gene either alone or together with other recombinant components.

3. A kit comprising a cell transfected with one or more polynucleotides according to the invention each encoding a different response element each one activated by a different pharmacologically active analyte following the interaction of the analyte with an intracellular or cell surface molecule, and a detection sequence unique to each polypeptide.

The invention also relates to a kit or a kit of parts. The kit may comprise:

i) a cell according to the invention;
; and
ii) an antibody directed against the anchor sequence that may be biotinylated or not
; and
iii) an antibody directed against the detection sequence that be labelled or not with HRP for detection by ELISA or with a Sulfo-Tag that permits detection of the secreted reporter-peptide on the MSD platform, or Alexa that permits detection on the Gyros platform, or digoxigenin that permits detection on the PerkinElmer AlphaLISA platform or unlabeled for analysis by SPR.
; and
iv) a streptavidin-coated microtiter plate, or a streptavidin-coated beads, or a streptavidin-coated SPR chip The kit may also comprise one or more vials, such as e.g. 2 or more vials etc of assay-ready frozen cells according to the invention either alone or together with the anchor and detection antibodies included in the frozen vial.

4. A method for quantifying the activity of a drug, whether a small molecule, large biopharmaceutical, AAV transgene, or cellular therapy such as CAR-T cells; or the antibody response to a protein-based drug, or AAV viral vector or AAV transgene, or cellular therapy such as CAR-T cells; or the effector cell function of a therapeutic antibody or Fc fusion protein, or cellular therapy ex vivo in clinical samples from patients treated with a therapeutic antibody, Fc fusion protein, or cellular therapy;

wherein the method may comprise the steps of;

contacting a sample, obtained from a patient undergoing treatment, with cells according to the invention.

harvesting the supernatant after an appropriate period of time addition of the anchor & detection antibodies analysis of the sample by ELISA or on the appropriate immuno-assay platform

The invention claimed is:

1. A polynucleotide comprising the following i) to iv) in the direction of 5' to 3':
   i) a response element that is capable of binding one or more transcription factors and is a 5-fold tandem repeat of gal4 upstream activation sequence (UAS),
   ii) a TATA box,
   iii) a sequence that encodes a reporter peptide and comprises any one of the sequences set forth in SEQ ID NOS.: 1-3, and
   iv) a polyadenylation sequence, and
      wherein the transcription factors in i) are chimeric transcription factors comprising the trans-activation domain of Elk-1 fused to a synthetic DNA binding domain capable of binding to the gal4 UAS cis-acting regulatory sequence of the secreted reporter peptide, and
      wherein the reporter peptide in iii) comprises a signal peptide, an anchor sequence and a detection sequence that are different from each other, and
      wherein the anchor sequence and the detection sequence are selected from c-MYC, V5 protein, or VSV-G protein, and
      wherein antibodies bind to the detection sequence and the anchor sequence.

2. The polynucleotide according to claim 1, wherein the expression of said polynucleotide in a cell is proportional to the activity of an analyte to be quantified,
   wherein said cell possesses an intracellular or cell surface molecule that will interact specifically with the analyte, and
   wherein quantification of the activity of the analyte is made by means of detection of secretion of a reporter peptide into a supernatant of said cell.

3. The polynucleotide according to claim 1, wherein quantification of the activity of an analyte is made by means of detection of secretion of a reporter/signal-peptide into a cell supernatant.

4. The polynucleotide according to claim 1, wherein detection of the reporter/signal peptide is made by using an ELISA or a commonly available immuno-detection platform.

5. A cell transfected with one or more polynucleotides of claim 1.

6. The cell according to claim 5, wherein the cell is transfected with more than one of the polynucleotides, and wherein each of the polynucleotides encodes different response elements and each one of the different response elements is activated by a different pharmacologically active analyte.

7. The cell according to claim 6, wherein the interaction of the analyte with an intracellular or cell surface molecule results in a detection sequence unique to each polypeptide (reporter peptide).

8. The cell according to claim 5, wherein the cell is
   a cell selected from a T or B lymphocyte, a monocyte or natural killer cell of human or animal origin naturally occurring or recombinant selected from:
   a CAR-T cell,
   or a cell line selected from: human Jurkat, Raji, HEK293, KHYG1, or murine RAW264.7 cell line, or
   an avian cell line such as DT-40 or MSB-1, or
   a previously established engineered cell line selected from a cell line containing a reporter-gene either alone or together with other recombinant components.

9. A kit comprising:
   i) a cell of claim 5;
   ii) an antibody directed against the anchor sequence that may be optionally biotinylated;
   iii) an antibody directed against the detection sequence that is optionally labelled with HRP for detection by ELISA or optionally with a Sulfo-Tag that allows for detection of the secreted reporter-peptide; and iv) a streptavidin-coated microtiter plate, streptavidin-coated beads, or a streptavidin-coated SPR chip.

10. The kit according to claim 9, wherein the anchor sequence or detection sequence are set forth in SEQ ID NOS.: 4-7.

11. The kit according to claim 9, wherein detection is made by a MSD platform, or Alexa that permits detection on a Gyros platform, or digoxigenin that permits detection on a PerkinElmer AlphaLISA platform or unlabeled for analysis by SPR.

12. The kit according to claim 9, comprising one or more vials,
comprising cells of claim 5, wherein the cells are assay-ready frozen cells, either alone or together with the anchor and detection antibodies, or
comprising cells of claim 5 together with a detection antibody alone in the case of the anchor sequence encoding streptavidin binding protein included in a frozen vial.

13. A method for quantifying expression of a reporter peptide, the method comprising the steps of:
contacting a sample, obtained from a patient treated with a drug, with cells of claim 5, wherein the drug is a small molecule, biopharmaceutical, AAV transgene, AAV viral vector, therapeutic antibody, Fc fusion protein, or cellular therapy;
harvesting the supernatant after an appropriate period of time;
adding anchor and detection antibodies; and
analysing the supernatant with added anchor and detection antibodies by ELISA or on an immuno-assay platform, and quantifying expression of the reporter peptide.

* * * * *

SEQUENCE LISTING

```
<160> NUMBER OF SEQ ID NOS: 7

<210> SEQ ID NO 1
<211> LENGTH: 997
<212> TYPE: DNA
<213> ORGANISM: Homo sapiens

<400> SEQUENCE: 1
actagtatta tgcccagtac atgaccttat gggactttcc tacttggcag tacatctacg    60
tattagtcat cgctattacc atggtgatgc ggttttggca gtacatcaat gggcgtggat   120
agcggtttga ctcacgggga tttccaagtc tccaccccat tgacgtcaat gggagtttgt   180
tttggcacca aaatcaacgg gactttccaa aatgtcgtaa caactccgcc ccattgacgc   240
aaatgggcgg taggcgtgta cggtgggagg tttatataag cagagctcgt ttagtgaacc   300
gtcagatcgc ctggagacgc catccacgct gttttgacct ccatagaaga ttctagagct   360
agccaccatg gctctgacat ttgctctgct ggtggccctg ctggtgctga gctgtaaaag   420
cagctgtagc gtgggcgacc tgcctcaaga gcagaagctg atctccgagg aagatctgac   480
ccacagcctg ggctctagac ggacactgat gctgctggcc cagatgcgga gaatcagcct   540
gttcagctgc ctgaaggacc ggcacgattt cggcttccct caagaggaat tcggcaacca   600
gttccagaag gccgagacaa tccctgtgct gcacgagatg atccagcaga tcttcaacct   660
gttctccacc aaggacagca gcgccgctgg caagcccatt cctaatcctc tgctgggcct   720
cgacagcacc tgagctagcg aattcgaatt taaatcggat ccgcggccgc gccagacatg   780
ataagataca ttgatgagtt tggacaaacc acaactagaa tgcagtgaaa aaaatgcttt   840
atttgtgaaa tttgtgatgc tattgcttta tttgtaacca ttataagctg caataaacaa   900
gttaacaaca acaattgcat tcattttatg tttcaggttc agggggaggt gtgggaggtt   960 tttttaaagca agtaaaacct ctacaaatgt ggtatgg                           997

<210> SEQ ID NO 2
<211> LENGTH: 1000
<212> TYPE: DNA
<213> ORGANISM: Homo sapiens

<400> SEQUENCE: 2
actagtatta tgcccagtac atgaccttat gggactttcc tacttggcag tacatctacg    60
tattagtcat cgctattacc atggtgatgc ggttttggca gtacatcaat gggcgtggat   120
agcggtttga ctcacgggga tttccaagtc tccaccccat tgacgtcaat gggagtttgt   180
tttggcacca aaatcaacgg gactttccaa aatgtcgtaa caactccgcc ccattgacgc   240
aaatgggcgg taggcgtgta cggtgggagg tttatataag cagagctcgt ttagtgaacc   300
gtcagatcgc ctggagacgc catccacgct gttttgacct ccatagaaga ttctagagct   360
```

-continued

```
agccaccatg gctctgacat tgctctgct  ggtggccctg ctggtgctga gctgtaaaag    420
cagctgtagc gtgggcgacc tgcctcagta caccgacatc gagatgaacc ggctgggcaa    480
gacacacagc ctgggctcta agaaccct   gatgctgctg cccagatgc  ggagaatcag    540 cctgttcagc tgcctgaagg accggcacga tttcggcttc cctcaagagg aattcggcaa    600
ccagttccag aaggccgaga caatccctgt gctgcacgag atgatccagc agatcttcaa    660
cctgttctcc accaaggaca gcagcgccgc tggcaagccc attcctaatc tctgctggg    720 cctcgacagc acctgagcta gcgaattcga atttaaatcg gatccgcggc cgcgccagac    780
atgataagat acattgatga gtttggacaa accacaacta gaatgcagtg aaaaaaatgc    840
tttatttgtg aaatttgtga tgctattgct ttatttgtaa ccattataag ctgcaataaa    900
caagttaaca acaacaattg cattcatttt atgtttcagg ttcaggggga ggtgtgggag    960
gttttttaaa gcaagtaaaa cctctacaaa tgtggtatgg                          1000
```

```
<210> SEQ ID NO 3
<211> LENGTH: 860
<212> TYPE: DNA
<213> ORGANISM: Homo sapiens

<400> SEQUENCE: 3
```

```
cggaggactg tcctccgagt ccggaggact gtcctccgag tccggaggac tgtcctccga     60
gtccggagga ctgtcctccg agtccggagg actgtcctcc gctcgaggat atcaagatct    120
ggcctcggcg gccaagctta gacactagag ggtatataat ggaagctcga cttccagctt    180
ggcaatccgg tactgttggt aaagccacca gcgtctaga  gctagccacc atggctctga    240
catttgctct gctggtggcc ctgctggtgc tgagctgtaa aagcagctgt agcgtgggcg    300
acctgcctca gagcagaag ctgatctccg aggaagatct gacccacagc ctgggctcta    360
gacggacact gatgctgctg cccagatgc  ggagaatcag cctgttcagc tgcctgaagg    420
accggcacga tttcggcttc cctcaagagg aattcggcaa ccagttccag aaggccgaga    480
caatccctgt gctgcacgag atgatccagc agatcttcaa cctgttctcc accaaggaca    540
gcagcgccgc tggcaagccc attcctaatc tctgctgggg cctcgacagc acctgagcta    600
gcgaattcga atttaaatcg gatccgcggc cgcgccagac atgataagat acattgatga    660
gtttggacaa accacaacta gaatgcagtg aaaaaaatgc tttatttgtg aaatttgtga    720
tgctattgct ttatttgtaa ccattataag ctgcaataaa caagttaaca acaacaattg    780
cattcatttt atgtttcagg ttcaggggga ggtgtgggag gttttttaaa gcaagtaaaa    840
cctctacaaa tgtggtatgg                                                860
```

```
<210> SEQ ID NO 4
<211> LENGTH: 9
<212> TYPE: PRT
<213> ORGANISM: Artificial sequence
<220> FEATURE:
<223> OTHER INFORMATION: Synthetic

<400> SEQUENCE: 4

Glu Glu Phe Gly Asn Tyr Thr Asp Ile
1               5
```

```
<210> SEQ ID NO 5
<211> LENGTH: 10
<212> TYPE: PRT
<213> ORGANISM: Artificial sequence
<220> FEATURE:
```

```
<223> OTHER INFORMATION: Synthetic

<400> SEQUENCE: 5

Ser Asp Val Glu Ala Trp Tyr Thr Asp Ile
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic

<400> SEQUENCE: 6

Pro Val Ala Leu Leu Glu Thr Thr Glu Thr His Ser Leu
1               5                   10

<210> SEQ ID NO 7
<211> LENGTH: 14
<212> TYPE: PRT
<213> ORGANISM: Artificial sequence
<220> FEATURE:
<223> OTHER INFORMATION: Synthetic

<400> SEQUENCE: 7

Pro Leu Ala Leu Leu Glu Met Ala Asn Asp Thr His Ser Leu
1               5                   10
```